United States Patent
Tsuji et al.

(10) Patent No.: US 6,677,124 B2
(45) Date of Patent: Jan. 13, 2004

(54) MONOCLONAL ANTIBODY RECOGNIZING C-TERMINUS OF HBNP

(75) Inventors: Tetsuo Tsuji, Nara (JP); Ken Inouye, Hyogo (JP); Akira Yamauchi, Osaka (JP); Masao Kono, Osaka (JP); Ken'ichi Igano, Nara (JP)

(73) Assignee: Shionogi Seiyaku Kabushiki Kaisha, Osaka (JP)

(*) Notice: Subject to any disclaimer, the term of this patent is extended or adjusted under 35 U.S.C. 154(b) by 202 days.

(21) Appl. No.: 09/942,709

(22) Filed: Aug. 31, 2001

(65) Prior Publication Data

US 2002/0025559 A1 Feb. 28, 2002

Related U.S. Application Data

(63) Continuation of application No. 08/749,031, filed on Nov. 14, 1996, now abandoned, and a continuation of application No. 08/236,013, filed on May 2, 1994, now abandoned, and a continuation of application No. 07/976,457, filed on Nov. 13, 1992, now abandoned.

(30) Foreign Application Priority Data

Nov. 14, 1991 (JP) .............................................. 3-326961

(51) Int. Cl.$^7$ ...................... G01N 33/53; G01N 33/567; A61K 39/395; A61K 39/40; C07K 16/00; C07K 17/00
(52) U.S. Cl. ...................... 435/7.1; 435/70.21; 435/7.2; 435/325; 435/326; 435/331; 435/336; 530/388.1; 530/329; 424/130.1; 424/139.1; 424/141.1; 424/158.1
(58) Field of Search ................................ 435/70.21, 325, 435/326, 331, 336, 7.2, 7.1; 530/329, 388.1; 424/130.1, 139.1, 141.1, 158.1

(56) References Cited

U.S. PATENT DOCUMENTS 5,786,163 A * 7/1998 Hall ........................... 435/7.92
6,124,430 A * 9/2000 Mischak et al. ............. 530/324
6,162,902 A * 12/2000 Mischak et al. ......... 530/388.24
6,376,207 B1 * 4/2002 Mischak et al. ............ 435/7.94

FOREIGN PATENT DOCUMENTS

EP          0306309 A2    8/1989

OTHER PUBLICATIONS

S. Hashida et al., Clinica Chimica Acta, 175 (1988) 11–18; "Enzyme immunoassay for alpha–human atrial natruuretic polypeptide—direct measurement of plasma level".
Bulinski, International Review of Cytology, vol. 103, pp. 281–302 (1986), "Peptide Antibodies: New Tools for Cell Biology".
Takeyama et al., J.Imm.Math, vol. 130 (1990), pp. 217–222.
Sutcliffe et al; Science, vol. 219 (1983), pp. 660–666.
Itoh et al., Endocrinology 127: pp. 1292–1300 (1990).
Takeyama et al., J.Imm.Meth. 130: pp. 217–222 (1990).
Sutcliffe et al., Science 219: pp. 660–666 (1983).
Harlow et al., Antibodies A Laboratory Manual (1988), Cold Spring Harbor Laboratory, pp. 578–582.
Mukoyama et al. (1990), The Lancet 335:801–802.
Mukoyama et al. (1991), J. Clin. Invest. 87:1402–1412.
Patent Abstracts of Japan (1992) vol. 16, No. 140, p. 22 C 962, No. 3–297–392.

* cited by examiner

*Primary Examiner*—Gary Kunz
*Assistant Examiner*—Christopher James Nichols
(74) *Attorney, Agent, or Firm*—Birch, Stewart, Kolasch & Birch, LLP

(57) ABSTRACT

A hybridoma producing a monoclonal antibody recognizing the C-terminus of human brain natriuretic peptide (hBNP) was cultivated in a medium or the abdominal cavity of a mouse to recover the monoclonal antibody from the medium or ascites accumulated in the abdominal cavity. An immunoassay for hBNP was established using the monoclonal antibody. The immunoassay for hBNP of the invention is so sensitive that the minimum detection limit is 1 pg/ml and can therefore determine the hBNP level in blood plasma directly, without the extraction of hBNP from blood plasma. It is useful for diagnosing diseases such as hypertension and the like, and states of the heart, kidney, and the like by using the increase/decrease of the hBNP level as an index.

19 Claims, 2 Drawing Sheets

MONOCLONAL ANTIBODY RECOGNIZING C-TERMINUS OF HBNP

This application is a continuation of application Ser. No. 08/749,031, filed on Nov. 14, 1996 now abandoned and application Ser. No. 08/236,013, filed on May 2, 1994 (now abandoned) and application Ser. No. 07/976,457, filed Nov. 13, 1992 (now abandoned), the entire contents of which are hereby incorporated by reference and for which priority is claimed under 35 U.S.C. §120; and this application claims priority of Application No. 3-326961 filed in Japan on Nov. 14, 1991 under 35 U.S.C. §119.

BACKGROUND OF THE INVENTION

1. Field of the Invention

This invention relates to a monoclonal antibody recognizing the C-terminus of hBNP, a hybridoma producing the monoclonal antibody, a method of producing the monoclonal antibody comprising cultivating the hybridoma in a medium or an abdominal cavity of a mouse and recovering said monoclonal antibody from said medium or ascites in said abdominal cavity, and an immunoassay for hBNP with use of said monoclonal antibody.

2. Related Art

Brain natriuretic peptide (BNP) in the porcine brain was first reported by Matsuo et al, Nature 332, 78–81 (1988). There exist porcine (p) BNP-26 of 26 amino acid residues and pBNP-32 of 32 residues. These has peripheral and central actions similar to those of atrium natriuretic peptide (ANP) and play an important role in the homeostasis of body fluid and the control of blood pressure together with ANP. BNP was suggested to be produced in and secreted from the heart in human (Biochem. Biophys. Res. Commun. 159, 1427–1434 (1989)), and BNP in the human heart has recently be isolated and characterized (FEBS Lett. 259, 341–345 (1990)). Human BNP (hBNP) comprises 32 amino acid residues identical with the sequence 77–108 of hBNP precursor.

SUMMARY

As mentioned above, because BNP plays an important role in the homeostasis of body fluid and the control of blood pressure, the determination of hBNP in the blood by an immunoassay etc. seems useful for diagnosing diseases such as hypertension and the like and states of heart, kidney and the like with taking an increase/decrease of hBNP level as an index. However, an average level of hBNP in the blood of normal adults is 0.9±0.07 fmol/ml (3.12±0.24 pg/ml) (J. Clin. Invest. 87, 1402–1412 (1991)) and such a low level has made it impossible to directly assay hBNP in the blood plasma without an extraction.

The inventors of this invention made an effort to solve the problem as mentioned above and succeeded in preparing a monoclonal antibody recognizing the C-terminus of hBNP and thereby establishing a specific sandwich radioimmunoassay for hBNP.

The immunoassay for hBNP provided by this invention is so sensitive that its minimum detection limit is 1 pg/ml and can therefore determine an hBNP level in plasma directly, that is, without extracting hBNP from plasma. It is useful for diagnosing diseases such as hypertension and the like and states of a heart, a kidney and the like with taking an increase/decrease of hBNP level as an index.

DETAILED DESCRIPTION OF THE INVENTION

Figure 1:
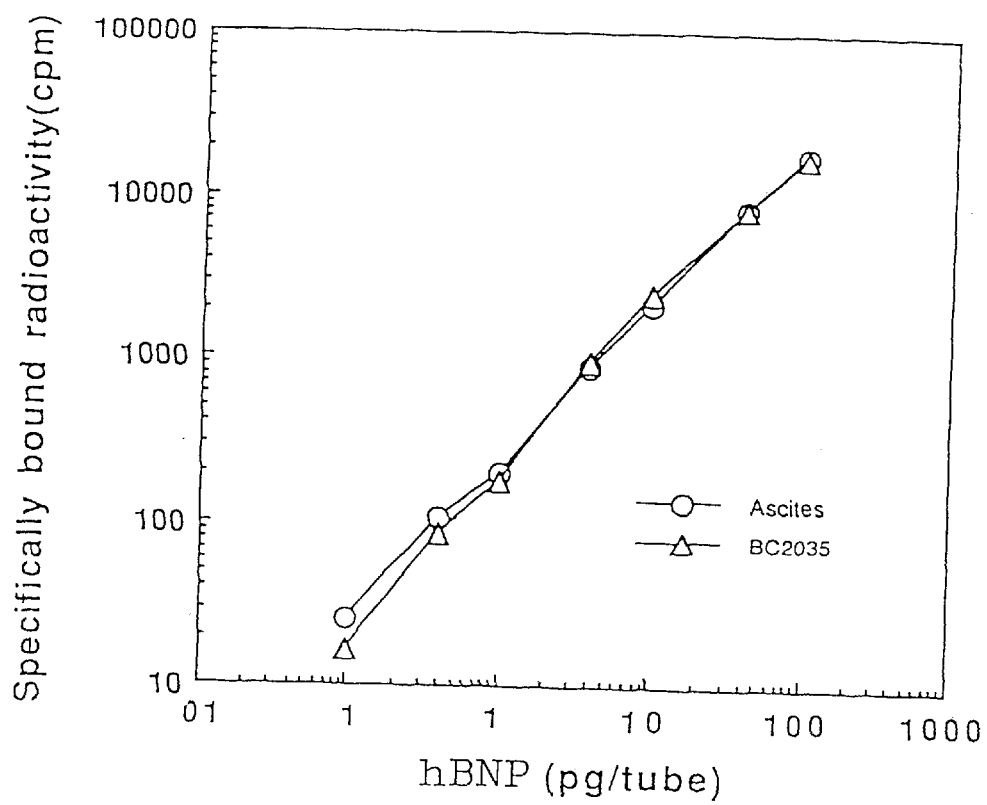
FIG. 1 shows a standard curve of the sandwich radioimmunoassay of this invention.

This invention provides a monoclonal antibody recognizing the C-terminus of hBNP and a hybridoma producing the same. The monoclonal antibody of this invention reacts with hBNP but not with hBNP having an additional Tyr residue at the C-terminus. It is unlikely that the monoclonal antibody reacts with hBNP having any additional amino acid residue except His at the C-terminus. Therefore, it is concluded that the monoclonal antibody of this invention mainly recognizes His residue at the C-terminus of hBNP, especially, a carboxyl group of the His residue.

The monoclonal antibody of this invention may be produced by a hybridoma BC203. This hybridoma BC203 has been deposited in the Fermentation Research Institute at 1-3, Higashi 1-chome, Tsukuba-shi, Ibaraki-ken, as Mouse Hybridoma BC203 with an accession number FERM BP-3515 under the Budapest Treaty since Aug. 20, 1991.

The hybridoma of this invention may be produced as follows. A peptide having a sequence around the C-terminus of hBNP, preferably hBNP(27–32), is prepared and conjugated to bovine serum albumin, bovine thyroglobulin or the like to increase its antigenicity. Thus obtained conjugate is emulsified with an appropriate adjuvant such as Freund's complete adjuvant to be used for the immunization of mice.

For the immunization the emulsion is intraperitoneally, intravenously or subcutaneously inoculated several times into mice at intervals of a few weeks. The spleen is excised 3–5 days after the last immunization to be used as antibody-producing cells. Thus obtained antibody-producing cells are fused with myeloma cells having an appropriate marker to prepare hybridomas.

A medium to be used for the preparation of hybridomas includes Eagle's MEM, Dulbecco's modified medium, RPMI-1640 and the like conventional. Myeloma cells are fused with spleen cells (myeloma cells:spleen cells=about 1:5). As to a fusing agent 50% of polyethyleneglycol (PEG) may preferably be chosen for higher yield of fusion cells. Fusion cells are selected according to the HAT method. Thus obtained hybridomas are screened by a competitive radioimmunoassay or the like using their cultivation supernatants to get hybridomas producing desired immunoglobulin. The obtained hybridomas were subcloned in order to make hybridomas monoclonal. In brief, they are sown in a 96-well plate at a concentration of less than one cell per well and clones grown are again screened. This subcloning is repeated to yield monoclonal hybridomas.

This invention further provides a method of producing the above-mentioned monoclonal antibody, which method comprises cultivating the above-mentioned hybridoma in a medium or in an abdominal cavity of a mouse and recovering said monoclonal antibody from said medium or from ascites accumulated in said abdominal cavity.

In brief, the above-mentioned hybridoma is cultivated in an incubator (in vitro) or in an animal (in vivo). For the in vitro system a medium may be selected from the conventional ones, as mentioned above, fortified with fetal calf serum (FCS), in which medium the hybridoma is cultivated for 3–5 days to recover the monoclonal antibody from the supernatant of the medium. For the in vivo system the hybridoma is inoculated into an abdominal cavity of a mammal and after 1–3 weeks ascites accumulated in the abdominal cavity is recovered, from which the monoclonal antibody is recovered. The in vivo system is preferable to the in vitro system because the monoclonal antibody can efficiently be produced in the in vivo system much more than in the in vitro system.

Monoclonal antibody BC203 of this invention recognizes hBNP at around the C-terminus. As described in the Example, BC203 does not bind to [$Tyr^{33}$]-hBNP, that is, hBNP which has additional Tyr residue at the C-terminus that is prepared by linking Tyr residue to the C-terminal residue $His^{32}$ of hBNP. This indicates that BC203 recognizes the C-terminal residue $His^{32}$ of hBNP.

This invention provides an immunoassay for hBNP characterized in that hBNP is sandwiched between the above-mentioned monoclonal antibody A and an antibody B which recognizes hBNP at the site different from that recognized by said antibody A. A preferable embodiment of said antibody B is a monoclonal antibody, especially, recognizing the ring structure of hBNP, for example, monoclonal antibody KY-hBNP-II (Japanese Patent Application No. 2-99623). The hybridoma KY-hBNP-II producing this antibody has been deposited in the Fermentation Research Institute at 1-3, Higashi 1-chome, Tsukuba-shi, Ibaraki-ken as Mouse Hybridoma KY-hBNP-II with an accession No. FERM BP-2863 under the Budapest Treaty since Apr. 11, 1990.

An immunoassay of this invention is briefly explained below with taking a sandwich radioimmunoassay as an example.

(1) Preparation of Antibody Labeled with Isotope

An IgG fraction of either of the above-mentioned antibodies A and B is digested with pepsin to give $F(ab')_2$ fragment, which is reduced with 2-mercaptoethanol to yield Fab' fragment. A method of preparing Fab' from IgG is detailed in J. Immunoassay 4, 209–327 (1983), which is also applicable to this invention. Fab' fragment thus obtained is labeled with an isotope according to the conventional methods such as Chloramine T method, a method using maleimide-monoiodo($^{125}$I)tyramine and the like. The labeled antibody is purified by gel filtration, column chromatography or the like.

(2) Preparation of Second Antibody Immobilized

According to the manner described in Japanese KOKAI 62-132172, an anti-mouse IgG Fc fragment antibody is immobilized on a commercially available carrier for an antigen-antibody reaction, such as beads, a ball, a tube or a plate made of glass or synthesized resin, which is usually used for the conventional immunoassays.

(3) Assay of hBNP

A standard solution or a sample of hBNP is allowed to react with the labeled antibody A or B (Fab') of the above step (1) and the other antibody B or A in a tube. The immobilized anti-mouse Fc of the above step (2) is added thereto to be allowed to react. After centrifugation, the supernatant is removed for washing. Radioactivity of the labeled antibody precipitated is determined.

Further, the antibody A or B different from the labeled antibody can be immobilized on a carrier and used as an immobilized antibody. In this case, hBNP is allowed to react with the labeled antibody A or B and the immobilized antibody B or A, respectively. After centrifugation the supernatant is removed for washing and radioactivity of the labeled antibody precipitated is determined.

The method of this invention includes not only radioimmunoassay but also enzyme immunoassay (EIA). An enzyme-conjugated antibody for EIA is prepared as follows.

An IgG fraction of either the above-mentioned antibody A or B is digested with pepsin to give $F(ab')_2$ fragment, which is reduced with 2-mercaptoethylamine to yield Fab' fragment. A method of preparing Fab' from IgG is detailed in J. Immunoassay 4, 209–327 (1983), which is also applicable to this invention.

The Fab' fragment thus obtained is conjugated with an enzyme. An enzyme to be conjugated includes alkaline phosphatase, β-D-galactosidase, peroxidase, glucose oxidase and so on. Horse radish peroxidase is preferably applied to the present method. A bridging agent to be used for the conjugation includes N,N'-o-phenylene-dimaleimide, 4-(N-maleimidomethyl)cyclohexanoic acid N-succinimide ester, 6-maleimidohexanoic acid N-succinimide ester, 3-(2-pyridylthio)-propionic acid N-succinimide ester, 4,4'-dithiopyridine and other well known bridging agents. These bridging agents can be used to conjugate an antibody with an enzyme according to the conventional methods suitable for the properties of the agents.

The present immunoassay is highly sensitive with the minimum detection limit being 1 pg/ml and extremely specific for hBNP, thereby enabling the direct assay of hBNP in blood plasma without an extraction.

The present invention is detailed in the following Example.

Abbreviation in the Example; Boc: t-butyloxycarbonyl, Tos: tosyl, PAM: 4-(oxymethyl)-phenylacetamidomethyl, Cl-Z: 2-chloro-benzyloxycarbonyl, Br-Z: 2-bromo-benzyloxycarbonyl, Bom: benzyloxymethyl, Bzl: benzyl, cHex: cyclohexyl, maleimide-monoiodo [$^{125}$I]tyramine: N-[2-4[-hydroxy-3([$^{125}$I]iode)phenyl]ethyl]-4-(maleimidomethyl)-1-cyclohexanecarboxamide.

EXAMPLE

I. Preparation of Hybridoma Producing Anti-hBNP Monoclonal Antibody and Production of Antibody (1) Preparation of Conjugate for Immunization Synthesis of hBNP fragment (27–32)

Boc-Lys(Cl-Z)-Val-Leu-Arg(Tos)-His(Tos)-PAM-Resin (SEQ ID NO: 3), wherein protected amino acids were purchased from Applied Biosystems, was synthesized from Boc-His(Tos)-PAM-Resin (Applied Biosystems)(0.25 mmol) by an amino acid synthesizer such as SHIONOGI SRL-02 according to the usual solid phase method. This was deprotected with HF/anisole. The crude peptide thus obtained was subjected to reversed phase chromatography (column:Wako Pure Chemical RQ-2,24×360 mm)with linear gradient of 0–50% $CH_3CN$/0.1% $CF_3COOH$ for purification to give 59 mg of the desired peptide.

The obtained preparation gave a single peak, retention time: 6.04 min, on analytical HPLC using a column of Nucleosil $5C_{18}$ (4.6×150 mm, Shinwa Chemical Industries Ltd.), under the condition of solvent: 5% $CH_3CN$/0.1% $CF_3COOH$, flow rate: 1.8 ml/min and detection: 220 nm.

The peptide was hydrolyzed with 6M HCl at 110° C. for 24 hr by HITACHI automatic amino acid analyzer Type 835 and the result of amino acid analysis of the hydrolyzate is described below.

Val 0.95(1); Leu 1.00(1); Lys 0.90(1); His 0.95(1); Arg 2.00(2)

Preparation of Conjugate

An aqueous solution of bovine thyroglobulin (40 mg/2.0 ml) was mixed with an aqueous solution of hBNP fragment (27–32) (16 mg/1.0 ml). To the mixture was added an aqueous solution of 1-ethyl-3(3-dimethylaminopropyl) carbodiimide hydrochloride (46 mg/0.6 ml) and stirred at 0° C. for 2 hr. The reaction mixture was dialyzed against distilled water at 4° C. for 2 days and the dialysate was lyophilized. A portion of the dialysate with or without being gel-filtrated was subjected to amino acid analysis to calculate the conjugation ratio, which was 29 molecules of hBNP fragment (27–32) per bovine thyroglobulin molecule.

(2) Immunization

A suspension of the obtained hBNP fragment (27–32)—bovine thyroglobulin conjugate in physiological saline (conjugate concentration: 4 mg/ml) was emulsified with an equal volume of Freund's complete adjuvant. The emulsion was subcutaneously injected 5 times to BALB/c mice (female, 6 weeks old) at intervals of 3 weeks at a dose of 0.1 ml. The amount injected to one mouse in one injection was 200 µg as the conjugate and 5.6 µg as the hapten hBNP fragment (27–32). Three weeks after the last immunization, 400 µg of hBNP fragment (27–32)—bovine thyroglobulin conjugate (11.2 µg of the hapten) was suspended in physiological saline and 0.1 ml of the suspension was intraperitoneally injected as a booster to each of the mice once a day for 2 consecutive days.

(3) Cell Fusion

The spleens of the mice were excised 3 days after the booster and the spleen cells were put in 0.17 M ammonium chloride solution with ice-cooling for 5 min to destroy erythrocytes. The remaining cells were suspended in RPMI 1640 medium to prepare a splenic lymphocyte preparation to be used for cell fusion. Splenic lymphocytes ($1.88 \times 10^8$) thus obtained were mixed with 8-azaguanine resistant myeloma cells (X63.653, $3.76 \times 10^7$) suspended in RPMI 1640 medium. After centrifugation the supernatant was removed, and to the cell precipitate was added 0.8 ml of 50% polyethyleneglycol (m.w. 4,000, Merck) in RPMI 1640 medium with agitation by a pipet in 1 min and further agitated for 1.5 min. Thereafter, 2 ml of RPMI 1640 medium was added in 2 min and then 2 ml in 1 min with agitation. Further, 18 ml of RPMI 1640 medium was added dropwise with gentle agitation. After centrifugation the supernatant was removed and the precipitated cells were suspended in 100 ml of HAT medium (20% FCS-RFMI 1640 medium with $1 \times 10^{-4}$ M hypoxanthine, $4 \times 10^{-7}$ M aminopterin and $1.6 \times 10^{-5}$ M thymidine), 0.1 ml of which was put in each well of seven 96-well cell culture plates (Costar Corporation). In each of the wells $5 \times 10^4$ cells of mouse spleen cells in 0.1 ml of HAT medium had previously been put as a feeder. Thereafter, the cells were incubated with exchanging a half amount of HAT medium into fresh one at intervals of a few days. The growth of hybridomas was observed about 10 days later. The number of wells where hybridomas grew was 670 (99.7%) in total.

(4) Selection of Hybridoma

Supernatants of wells in which hybridomas grew were assayed for the production of anti-hBNP antibody according to the competitive radioimmunoassay. In brief, 50 µl of a supernatant was mixed in a tube with 150 µl of Assay buffer (described later in item V) and 100 µl of $^{125}$I-labeled hBNP (described in item V) diluted with Assay buffer by about 15,000 cpm/tube and was incubated at 4° C. for at least 16 hr. Then, 100 µl of 2.5% bovine gamma-globulin and 500 µl of 25% polyethyleneglycol 6000 (Yoneyama Yakuhin Kogyo Co., Ltd.) were added thereto, agitated and centrifuged at 3,000 rpm for 20 min. The supernatant was removed and radioactivity in the precipitate was determined by a gamma counter (Aloka ARC-600). Radioactivity of at least 5,000 cpm (about 5 times as much as nonspecific binding) was taken as positive to select 10 wells in total.

(5) Cloning

Hybridomas selected in item (4) were cloned by the limiting dilution method. They were incubated in 96-well cell culture plates at a concentration of 1 cell/200 µl/well. The supernatants of wells in which hybridomas grew were subjected to the radioimmunoassay of item (4). Hybridomas of antibody-positive wells were expanded. A series of these steps was repeated a few times to establish antibody-producing cell line BC203.

(6) Preparation of Ascites

The hybridoma thus established was transplanted into an abdominal cavity to prepare ascites of high antibody-concentration. Briefly, about $1 \times 10^7$ hybridomas suspended in RPMI 1640 were injected intraperitoneally to a mouse (male BALB/c) to which 0.5 ml of pristane had previously been injected intraperitoneally. Ascites was recovered at an appropriate timing during 1–3 weeks after the injection. After removing cells in the ascites by centrifugation, the obtained supernatant to which 0.1% sodium azide was added was kept frozen. Thus, the ascites BC203A containing monoclonal antibody BC203 produced by the hybridoma BC203 was obtained.

II. Determination of Class/Subclass of Monoclonal Antibody

Class/subclass of the monoclonal antibody produced by the hybridoma was determined by the immunodiffusion method using antibodies specific to each class/subclass of mouse immunoglobulins (Serotec, Mouse monoclonal antibody-typing kit). As a result, a precipitation line was observed between ascites BC203A and anti-IgG$_1$ antibody, indicating that the antibody BC203 belongs to IgG$_1$.

III. Determination of Affinity (Binding Constant) of Monoclonal Antibody

A standard curve for hBNP was made by the method described in item V. According to the Scatchard's method radioactivity of precipitate/radioactivity of supernatant was plotted in vertical axis and a molar concentration of antibody bound to antigen in horizontal axis on each concentration of hBNP. The binding constant of the antibody was determined to be $1.3 \times 10^9$ M$^{-1}$ from the inclination of thus obtained line.

IV. Specificity of Monoclonal Antibody (1) Synthesis of Tyr$^{33}$-$^{125}$I-Labeled hBNP Purified Tyr$^{33}$-hBNP (7.0 mg) was prepared from Boc-Tyr(Br-Z)-PAM-Resin (Applied Biosystems, 0.25 mmol Tyr) according to the synthesis of Tyr$^0$-hBNP-32 in the Referential Example using an amino acid synthesizer Applied Biosystems 430A, and was labeled in the same manner as in the Referential Example to give the desired compound.

The obtained preparation gave a single peak (Retention time: 5.98 min) under the condition of column: YMC A-302 S-5 120A ODS, 4.6×150 mm (YMC Co., Ltd.); Solvent: 19.0% CH$_3$CN/0.1% CF$_3$COOH; Flow Rate: 1.0 ml/min; and Detection: 220 nm. A portion of the obtained preparation was hydrolyzed with 6 M HCl at 110° C. for 20 h in the presence of phenol and subjected to an amino acid analysis to give the following result.

Asp 1.05(1); Ser 5.46(6); Glu 1.04(1); Gly 5.21(5); Val 1.97(2); Met 1.94(2); Ile 0.97(1); Leu 2.00(2); Tyr 1.01(1); Phe 1.00(1); Lys 3.01(3); His 0.95(1); Arg 3.88(4); Pro 1.05(1)

(2) Specificity of Antibody

Tyr$^{33}$-$^{125}$I-labeled hBNP, wherein an additional Tyr residue was introduced into the C-terminal His residue of hBNP, did not bind to the monoclonal antibody of this invention in the radioimmunoassay of item I-(4), indicating that the monoclonal antibody of this invention specifically binds to hBNP at the C-terminal His residue.

V. Sandwich Radioimmunoassay for hBNP Using Monoclonal Antibody (Direct Method)

Sandwich radioimmunoassay for hBNP was established using the monoclonal antibody BC203 described in item I and $^{125}$I-labeled Fab' of anti-hBNP(1–32) antibody (hereinafter referred to as KY-hBNP-II) produced by hybridoma KY-hBNP-II (Japanese Patent Application No. 2-99623).

(1) Synthesis of $^{125}$I-labeled KY-hBNP-II Fab'

Purification of Ascites: Ascites (3 ml) from hybridoma KY-hBNP-II was purified by Protein G sepharose 4FF, MAb TrapTM G (Pharmacia). Ascites was 2-fold diluted with Binding Buffer (attached to Protein G sepharose 4FF, MAb TrapTM G Kit) and loaded on Protein G sepharose 4FF column (3 ml) previously equilibrated with Binding Buffer. Impurities other than IgG was removed by washing with 30 ml of Binding Buffer. After fractionation with 15 ml of Eluting Buffer (attached to Protein G sepharose 4FF, MAb TrapTM G Kit) to give 1 ml-fractions, IgG fractions were collected according to absorbance of at least 0.2 at 280 nm and concentrated by Centricon-100™ (Amicon). The buffer was exchanged into 0.1 M citrate buffer (pH 4.1) to give 18 mg of IgG fraction.

Preparation of F(ab')$_2$: To an IgG solution of KY-hBNP-II (4.57 mg/2.19 ml) as obtained above was added pepsin (porcine gastric mucosa, Sigma) by 2.5%(W/V) and then sodium chloride by 0.1 M. After 1 hr incubation at 37° C., the mixture was gel-filtrated with Sephadex G-100 column (1.5×58 cm)(Bio-Rad) equilibrated with 0.1 M sodium borate buffer (pH 8.0) to give F(ab')$_2$. Indigested IgG contained therein was removed by Affigel Protein A MAPS-II (Bio-Rad) for purification. In brief, fractions not adsorbed on Affigel Protein A were collected and concentrated by Centricon-30M (Amicon). The buffer was exchanged into 0.1 M sodium phosphate buffer (pH 6.0) containing 5 mM EDTA to give 1.4 mg of F(ab')$_2$ fraction.

Preparation of Fab': To an F(ab')$_2$ solution of KY-hBNP-II (0.4 mg/70 µl) was added 0.1 M 2-mercaptoethylamine hydrochloride (in 0.1 M sodium phosphate buffer (pH 6.0) containing 5 mM EDTA) to give a final concentration of 10 mM. After 90 min incubation at 37° C., the mixture was filtrated with TSK gel 2000XL (0.78×30 cm, TOSOH CORPORATION) equilibrated with 0.1 M sodium phosphate buffer (pH 6.0) containing 5 mM EDTA to give Fab' preparation. The Fab' preparation was concentrated to 60 µl with Centricon-30™ (Amicon) to prepare Fab' fraction (0.2 mg/60 µl).

Preparation of Maleimide-monoiodo($^{125}$-I)tyramine: Maleimidotyramine (15 µl, 1 mg/ml DMSO) was put in a glass tube, to which 60 µl of 0.2 M sodium phosphate buffer (pH7.0) and 208 MBq (5.6 mCi) of Na$^{125}$I were added. After addition of 10 µl of 0.5% chloramine T in 0.2 M sodium phosphate buffer (pH 7.0), the mixture was vigorously agitated for 30 sec and then subjected to a reversed phase HPLC using Nucleosil 10C18 column (0.46×30 cm) equilibrated with a reversed phase HPLC developing solvent (0.1% TFA:CH$_3$CN: CH$_3$OH=5:3:2) to collect Maleimide-monoiodo($^{125}$I)tyramine fractions. The fractions were evaporated to dryness under nitrogen atmosphere at 60° C. and then dissolved in 50 µl of 0.1 M sodium phosphate buffer (pH 6.0) containing 2% dimethyl sulfoxide (DMSO) and 5 mM EDTA.

$^{125}$I-Labeling of KY-hBNP-II Fab': KY-hBNP-II Fab' (70 µg) was put in a glass tube, to which 130 MBq of maleimide-monoiodo($^{125}$I)tyramine was added, followed by 90 min incubation at room temperature. To the mixture was added 0.1 M sodium phosphate buffer (pH 6.0) containing 1% S-carboxymethyl BSA, 0.02% N-ethylmaleimide and 5 mM EDTA. The resulting mixture was gel-filtrated with PD-10 (Sephadex G10, Bio-Rad) column equilibrated with 0.1 M sodium phosphate buffer (pH 6.0) containing 5 mM EDTA, and then with Superose 12 column (Pharmacia, 1.0×30 cm) equilibrated with 0.1 M sodium phosphate buffer (pH 6.0) containing 5 mM EDTA for purification of labeled antibody. The filtrate was put in glass tubes each containing 10 µl of 1% S-carboxymethyl BSA solution to give a fraction of purified $^{125}$I-KY-hBNP-II Fab' (about 26–40 MBq, i.e., 0.7–1.1 mCi).

(2) Preparation of Immobilized Second Antibody

Anti-mouse IgG Fc fragment rabbit serum (Rockland) was immobilized on Immunobeads matrix (Bio-Rad) according to the method described in Japanese Kokai No. 62-132172.

(3) Reagents

Assay buffer: 0.1 M phosphate buffer (pH 7.0) containing 0.372 g disodium ethylenediaminetetraacetate, 0.063 g cystine dihydrochloride, 0.1 g sodium azide, 10$^6$ KIU aprotinin and 1 g bovine serum albumin each per liter.

Diluted ascites: BC203A 1000-fold diluted with Assay Buffer.

hBNP standard: 1, 4, 10, 40, 100, 400 and 1000 pg of hBNP in 1 ml of Assay buffer.

(4) Method

In Shionogi tube (trade name) were put 100 µl of hBNP standard, 100 µl of $^{125}$I-labeled KY-hBNP-II Fab' and 100 µl of Diluted ascites (BC203A). After at least 16 h incubation at 4° C., a suspension (0.1 ml) of anti-mouse IgG Fc fragment rabbit serum immobilized on Immunobeads (2 mg/ml) was added and incubated at 4° C. for 4 h. After centrifugation at 3,000 rpm for 10 min, the supernatant was removed and the precipitate was washed with 1 ml of Washing solution (0.01M phosphate buffer, pH 7.0, containing 0.1% Tween-80 and 0.9% sodium chloride). After 10 min centrifugation at 3,000 rpm, the supernatant was removed and radioactivity of the precipitated $^{125}$I-labeled antibody was determined by a gamma counter (Aloka ARC-600).

(5) Standard Curve

A typical standard curve of the sandwich radioimmunoassay is shown in FIG. 1. It showed good linearity in the assay range from 1 pg/ml to 1,000 pg/ml. The minimum detection limit was 1 pg/ml. In FIG. 1, -○- (Ascites) shows a standard curve obtained by the above-mentioned method and -Δ- (BC2035) shows a standard curve obtained by the same method as mentioned above except the use of a monoclonal antibody from a supernatant of in vitro culture of hybridoma BC203 in place of Diluted ascites (BC203A).

(6) Plasma hBNP Levels in Healthy Subjects

Plasma hBNP levels in healthy subjects were determined by the immunoassay (direct method) of this invention and ranged from 1 pg/ml to 15 pg/ml as shown in Table 1, which was enough within the range detectable by the immunoassay of this invention.

TABLE 1

| Plasma No. | hBNP level (pg/ml) |
|---|---|
| 1 | 10.9 |
| 2 | 3.7 |
| 3 | 5.3 |
| 4 | 6.1 |
| 5 | 8.0 |
| 6 | 4.8 |
| 7 | 1 |
| 8 | 2.2 |
| 9 | 2.7 |
| 10 | 13.9 |
| 11 | 12.8 |
| 12 | 14.7 |

TABLE 1-continued

| Plasma No. | hBNP level (pg/ml) |
|---|---|
| 13 | 2.0 |
| 14 | 5.1 |
| 15 | 5.2 |

(7) Comparison between Direct and Extraction Methods

A comparison was made between the direct method of this invention which directly assays BNP in plasma and the extraction method which assays BNP in extract from plasma indirectly. For the extraction method, BNP was extracted from plasma with Sep-pak $C_{18}$ cartridge (trade name, Waters) and thereafter assayed by the same method as the above-mentioned sandwich radioimmunoassay. As shown in Table 2, values determined by the direct method and the extraction method showed good correlativity (coefficient of correlation: r=0.98). The direct method of this invention showed good enough sensitivity and reliability even without extraction of BNP and is a very simple method in comparison with the extraction method.

TABLE 2

| | hBNP level (pg/ml) | |
|---|---|---|
| Plasma No. | Extraction Method | Direct Method |
| 1 | 57.6 | 71.9 |
| 2 | 175 | 196 |
| 3 | 548 | 650 |
| 4 | 17.0 | 24.9 |
| 5 | 1,040 | 1,117 |
| 6 | 1,191 | 1,120 |
| 7 | 4.8 | 4.2 |
| 8 | 344 | 400 |
| 9 | 1,273 | 969 |
| 10 | 769 | 833 |
| 11 | 14.5 | 12.8 |
| 12 | 2.3 | 2.0 |
| 13 | 5.1 | 5.2 |

Referential Example

Radioimmunoassay Using Monoclonal Antibody

Competitive radioimmunoassay was carried out with use of the monoclonal antibody of this invention.

(1) Synthesis of $^{125}$I-labeled hBNP

Synthesis of Tyr$^0$-hBNP-32

Because hBNP has no Tyr residue to be labeled, Tyr$^0$-hBNP, i.e., hBNP having additional Tyr residue at the N-terminus, was synthesized. Namely, Boc-Tyr(Br-Z)-Ser(Bzl)-Pro-Lsy(Cl-Z)-Met-Val-Gln-Gly-Ser(Bzl)-Gly-Cys(4-CH$_3$OBzl)-Phe-Gly-Arg(Tos)-Lys(Cl-Z)-Met-Asp(OcHex)-Arg-Ile-Ser(Bzl)-Ser(Bzl)-Ser(Bzl)-Ser(Bzl)-Gly-Leu-Gly-Cys(4-CH$_3$OBzl)-Lys(Cl-Z)-Val-Leu-Arg(Tos)-Arg(Tos)-His(Bom)-PAM-resin (SEQ ID NO:1 was synthesized from 0.45 mmol of Boc-His(Bom)-PAM-resin (NOVA Biochem AG) according to the usual solid phase method using an amino acid synthesizer, Applied Biosystems 430A. A half amount of the obtained peptide was deprotected with HF/p-crezole/dimethylsulfide and diluted with distilled water. After adjusting pH to 9 with aqueous ammonium, the mixture was agitated at room temperature for 24 h to introduce a S—S bridge. Thus obtained crude peptide was subjected to reversed phase chromatography (column: YMC S-50 120A ODS AM-type, 30×200 mm) with a linear gradient of 0–40% CH$_3$CN/0.1% CF$_3$COOH, then to HPLC fractionation (column: μ-bondasphere 15C18 300A, 30×300 mm (Waters)) with a linear gradient of 12–22% CH$_3$CIN/0.1% CF$_3$COOH, and further purified by means of a column of YMC 342-5 S-5 120A ODS (20×150 mm) with a solvent of 19.5% CH$_3$CN/0.1% CF$_3$COOH to give 3.9 mg of the desired peptide.

Thus obtained preparation of the desired peptide gave a single peak (retention time: 9.10 min) on analytical HPLC (column: Cosmosil 5C$_{18}$, 4.6×150 mm (NACALAI TESQUE, INC.); solvent: 20% CH$_3$CN/0.1% CF$_3$COOH; flow rate: 1.0 ml/min; detection: 220 nm).

The peptide was hydrolyzed with 6 M HCl at 110° C. for 20 h in the presence of phenol and subjected to amino acid analysis to give the following result.

Asp 0.99(1): Ser 4.98(6); Glu 0.97(1); Gly 4.75(5); Val 1.90(2); Met 1.82(2); Ile 0.95(1); Leu 2.02(2): Tyr 0.85(1); Phe 0.93(1); Lys 2.79(3); His 1.00(1); Arg 3.78(4); Pro 0.89(1).

(Theoretical values in parentheses and an uncorrected value for Ser)

Labeling by Na $^{125}$I

Tyr$^0$-hBNP (10 μg) was mixed with 0.05 ml of 0.5 μM phosphate buffer (pH 7.5) and 18.8 MBq. of Na$^{125}$I (Amersham). To the mixture was added 0.01 ml of 0.2% chloramine T, followed by 30 sec agitation. The mixture was mixed with 1% sodium metabisulfite, to which 0.01 ml of 10% potassium iodide was added. The resulting mixture was subjected to HPLC (Column: YMC-A-302 S-5 12A ODS, 4.6×150 mm) with a gradient elution by CH$_3$CN/CF$_3$COOH to give 4.2 Mbeq. of the labeled peptide as a monoiodo form at a retention time of 19 min.

(2) Reagents

Assay buffer: 0.1 M phosphate buffer (pH 7.0) containing 0.372 g disodium ethylenediaminetetraacetate, 0.063 g cystine dihydrochloride, 0.1 g sodium azide, $10^6$ KIU aprotinin and 1 g bovine serum albumin each per liter.

Diluted ascites: BC203A 42,000-fold diluted with Assay Buffer hBNP standard: 3-fold serial dilutions (0.046–99.9 ng/ml) of commercially available hBNP (Peptide Institute, Inc.) with Assay buffer.

2.5% bovine gammaglobulin: bovine gammaglobulin dissolved in Assay buffer.

25% polyethyleneglycol: polyethyleneglycol 6000 (Yoneyama Yakuhin Kogyo Co., Ltd.) dissolved in Assay buffer without bovine serum albumin.

(3) Method

To Shionogi tube containing 100 μl of hBNP standard or a sample, 100 μl of $^{125}$I-labeled hBNP and 100 μl of Diluted Ascites were added, mixed and incubated at 4° C. overnight. Then, 100 μl of 2.3% bovine gammaglobulin cooled to 4° C. and 500 μl of 25% polyethyleneglycol were added and agitated immediately thereafter. After a centrifugation at 4° C. at 3,000 rpm for 20 min, the supernatant was removed and radioactivity in the precipitate was determined by a gamma counter (Aloka ARC-600).

(4) Standard Curve

Figure 2:
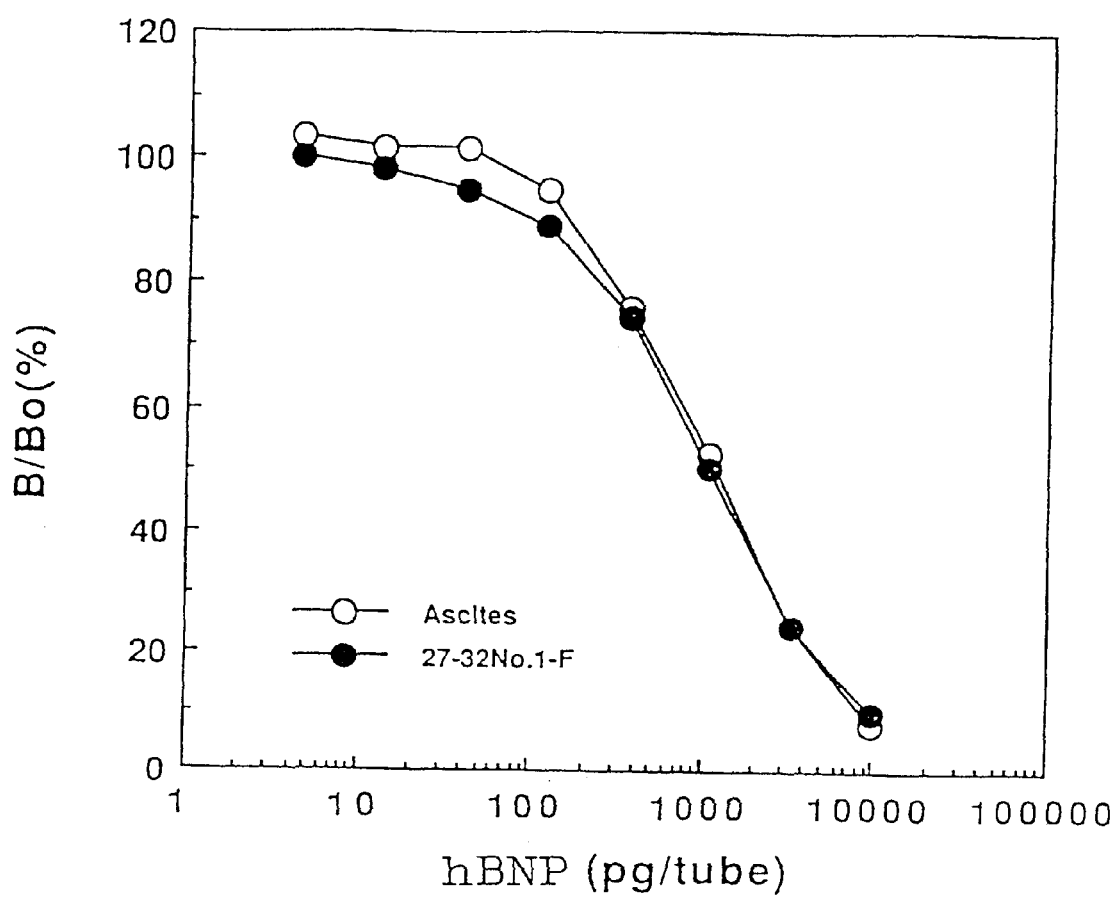
FIG. 2 shows a standard curve of the competitive radioimmunoassay using the monoclonal antibody of this invention.

A standard curve of this radioimmunoassay was shown in FIG. 2. Sensitivities as 90% and 50% inhibitory concentrations were 1.3 ng/ml and 11.8 ng/ml, respectively. In FIG. 2, -◯- (Ascites) indicates the standard curve obtained by the above-mentioned method and -●- (27–32 No. 1-F) indicates that obtained by the same as the above-mentioned method except the use of the final antiserum of the mouse immunized by hBNP(27–32) in place of Diluted ascites.

What we claimed is:

1. A monoclonal antibody that binds an epitope presented by an amino acid sequence lys-val-leu-arg-arg-his (SEQ ID NO:2) in the C-terminal region of human brain natriuretic peptide.

2. The monoclonal antibody of claim 1, which is produced by hybridoma BC203, FERM BP-3515.

3. A hybridoma which produces said monoclonal antibody of claim 1.

4. The hybridoma of claim 3, which is hybridoma BC203, FERM BP-3515.

5. A method of producing said monoclonal antibody of claim 1, which comprises cultivating a hybridoma which produces said monoclonal antibody in a medium or in the abdominal cavity of a mouse, and recovering said monoclonal antibody from said medium or from ascites in said abdominal cavity.

6. The method of claim 5, wherein said hybridoma is hybridoma BC203, FERM BP-3515.

7. An immunoassay for human brain natriuretic peptide, hBNP, comprising the steps of:

(a) immobilizing a first antibody which binds to an epitope presented by an amino acid sequence lys-val-leu-arg-arg-his (SEQ ID NO:2) in the C-terminal region of hBNP onto a solid phase to produce an immobilized antibody;

(b) contacting a solution suspected of containing hBNP with a second, enzyme-conjugated antibody or a radioisotope-labeled antibody, which recognizes the N-terminal region of hBNP, so as to allow the formation of hBNP-second antibody complexes;

(c) contacting said second antibody-hBNP complexes with said immobilized first antibody, to form immobilized first antibody-hBNP-second antibody complexes, removing the supernatant and washing said immobilized first antibody-hBNP-second antibody complexes;

(d) when an enzyme-conjugated antibody is employed in step (b), contacting the washed complexes of step (c) with a substrate of said enzyme in an appropriate reaction buffer and incubating so as to allow formation of the enzymatic reaction end-product;

(e) determining the amount of said end-product formed in step (d) when an enzyme-conjugated antibody is employed in step (b), or determining the amount of radioactivity bound to said solid phase when a radioisotope labeled antibody is employed in step (b); and (f) relating the amount of said end-product formed or the amount of radioactivity bound to said solid phase to the amount of said hBNP via the use of a standard curve for hBNP.

8. The immunoassay of claim 7, wherein said first antibody is produced by hybridoma BC203, FERM BP-3515.

9. The immunoassay of claim 7, wherein said second antibody is a monoclonal antibody.

10. The immunoassay of claim 9, wherein said second antibody recognizes the intramolecular disulfide bridged loop structure of hBNP.

11. The immunoassay of claim 10, wherein said second antibody is produced by hybridoma KY-hBNP-II, FERM BP-2863.

12. The immunoassay of claim 9, wherein hBNP in human blood plasma is directly assayed without extraction of said hBNP from said plasma.

13. A kit for immunoassay of hBNP, which comprises the monoclonal antibody of claim 1 and a second antibody which recognizes a region of hBNP different from that recognized by said monoclonal antibody.

14. The kit of claim 13, wherein said second antibody recognizes the intramolecular disulfide bridged loop structure of hBNP.

15. The kit of claim 13, wherein said second antibody is produced by hybridoma KY-hBNP-II, FERM BP-2863.

16. A monoclonal antibody that binds an epitope presented by an amino acid sequence lys-val-leu-arg-arg-his (SEQ ID NO:2) in the C-terminal region of human brain natriuretic peptide, hBNP, wherein the epitope includes the C-terminal his residue.

17. An immunoassay for human brain natriuretic peptide, hBNP, comprising:

(a) immobilizing a first antibody that binds to an epitope presented by the amino acid sequence lys-val-leu-arg-arg-his (SEQ ID NO:2) in the C-terminal region of hBNP, which epitope includes the C-terminal his residue, on a solid phase to produce an immobilized antibody;

(b) contacting a solution suspected of containing hBNP with a second, enzyme-conjugated antibody or a radioisotope-labeled antibody, which recognizes the N-terminal region of hBNP, so as to allow the formation of hBNP-second antibody complexes;

(c) contacting said second antibody-hBNP complexes with said immobilized first antibody, to form immobilized first antibody-hBNP-second antibody complexes, removing the supernatant and washing said immobilized first antibody-hBNP-second antibody complexes;

(d) when an enzyme-conjugated antibody is employed in step (b), contacting the washed complexes of step (c) with a substrate of said enzyme in an appropriate reaction buffer and incubating so as to allow formation of the enzymatic reaction end-product;

(e) determining the amount of said end-product formed in step (d) when an enzyme-conjugated antibody is employed in step (b), or determining the amount of radioactivity bound to said solid phase when a radioisotope labeled antibody is employed in step (b); and (f) relating the amount of said end-product formed or the amount of radioactivity bound to said solid phase to the amount of said hBNP by a standard curve for hBNP.

18. The immunoassay of claim 17, wherein said first antibody is produced by hybridoma BC203, FERM BP-3515.

19. An immunoassay for human brain natriuretic peptide, hBNP, comprising the steps of:

(a) immobilizing a first antibody which binds to an epitope presented by the amino acid sequence lys-val-leu-arg-arg-his (SEQ ID NO:2) in the C-terminal region of hBNP onto a solid phase to produce an immobilized antibody;

(b) contacting a solution suspected of containing hBNP with a second antibody, which recognizes the N-terminal region of hBNP, so as to allow the formation of hBNP-second antibody complexes;

(c) contacting said second antibody-hBNP complexes with said immobilized first antibody, to form immobilized first antibody-hBNp-second antibody complexes, removing the supernatant and washing said immobilized first antibody-hBNP-second antibody complexes;

(d) determining the amount of said first antibody-hBNP-second antibody complexes formed in step (c) and (e) relating the amount of said first antibody-hBNp-second antibody complexes formed to the amount of said hBNP via the use of a standard curve for hBNP.

* * * * *

SEQUENCE LISTING

<160> NUMBER OF SEQ ID NOS: 3

<210> SEQ ID NO 1
<211> LENGTH: 33
<212> TYPE: PRT
<213> ORGANISM: Artificial Sequence
<220> FEATURE:
<223> OTHER INFORMATION: synthetic amino acid according to the usual
      solid phase method
<220> FEATURE:
<221> NAME/KEY: SITE
<222> LOCATION: (1)..(1)
<223> OTHER INFORMATION: N-terminal BOC modified side chain Br-Z
      modified
<220> FEATURE:
<221> NAME/KEY: SITE
<222> LOCATION: (2)..(2)
<223> OTHER INFORMATION: side chain Bzl modified
<220> FEATURE:
<221> NAME/KEY: SITE
<222> LOCATION: (4)..(4)
<223> OTHER INFORMATION: side chain Cl-Z modified
<220> FEATURE:
<221> NAME/KEY: SITE
<222> LOCATION: (9)..(9)
<223> OTHER INFORMATION: side chain Bzl modified
<220> FEATURE:
<221> NAME/KEY: SITE
<222> LOCATION: (11)..(11)
<223> OTHER INFORMATION: side chain 4-CH3OBzl modified
<220> FEATURE:
<221> NAME/KEY: SITE
<222> LOCATION: (14)..(14)
<223> OTHER INFORMATION: side chain TOS modified
<220> FEATURE:
<221> NAME/KEY: SITE
<222> LOCATION: (15)..(15)
<223> OTHER INFORMATION: side chain Cl-Z modified
<220> FEATURE:
<221> NAME/KEY: SITE
<222> LOCATION: (17)..(17)
<223> OTHER INFORMATION: side chain OcHex modified
<220> FEATURE:
<221> NAME/KEY: SITE
<222> LOCATION: (20)..(20)
<223> OTHER INFORMATION: side chain Bzl modified
<220> FEATURE:
<221> NAME/KEY: SITE
<222> LOCATION: (21)..(21)
<223> OTHER INFORMATION: side chain Bzl modified
<220> FEATURE:
<221> NAME/KEY: SITE
<222> LOCATION: (22)..(22)
<223> OTHER INFORMATION: side chain Bzl modified
<220> FEATURE:
<221> NAME/KEY: SITE
<222> LOCATION: (23)..(23)
<223> OTHER INFORMATION: side chain Bzl modified
<220> FEATURE:
<221> NAME/KEY: SITE
<222> LOCATION: (27)..(27)
<223> OTHER INFORMATION: side chain 4-CH3OBzl modified
<220> FEATURE:
<221> NAME/KEY: SITE
<222> LOCATION: (28)..(28)
<223> OTHER INFORMATION: side chain Cl-Z modified
<220> FEATURE:
<221> NAME/KEY: SITE
<222> LOCATION: (31)..(31)
<223> OTHER INFORMATION: side chain TOS modified
<220> FEATURE:
<221> NAME/KEY: SITE
<222> LOCATION: (32)..(32)
<223> OTHER INFORMATION: side chain TOS modified
<220> FEATURE:
<221> NAME/KEY: SITE

```
<222> LOCATION: (33)..(33)
<223> OTHER INFORMATION: side chain Bom modified

<400> SEQUENCE: 1

Tyr Ser Pro Lys Met Val Gln Gly Ser Gly Cys Phe Gly Arg Lys Met
1               5                   10                  15
Asp Arg Ile Ser Ser Ser Ser Gly Leu Gly Cys Lys Val Leu Arg Arg
            20                  25                  30
His

<210> SEQ ID NO 2
<211> LENGTH: 6
<212> TYPE: PRT
<213> ORGANISM: Homo sapiens

<400> SEQUENCE: 2

Lys Val Leu Arg Arg His
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic amino acid according to the usual
      solid phase method
<220> FEATURE:
<221> NAME/KEY: SITE
<222> LOCATION: (1)..(1)
<223> OTHER INFORMATION: N-terminal BOC modified side chain Cl-Z
      modified
<220> FEATURE:
<221> NAME/KEY: SITE
<222> LOCATION: (4)..(4)
<223> OTHER INFORMATION: side chain TOS modified
<220> FEATURE:
<221> NAME/KEY: SITE
<222> LOCATION: (5)..(5)
<223> OTHER INFORMATION: side chain TOS modified

<400> SEQUENCE: 3

Lys Val Leu Arg His
1               5
```